(12) United States Patent
Baumann et al.

(10) Patent No.: US 7,817,777 B2
(45) Date of Patent: Oct. 19, 2010

(54) FOCUS DETECTOR ARRANGEMENT AND METHOD FOR GENERATING CONTRAST X-RAY IMAGES

(75) Inventors: Joachim Baumann, München (DE); Christian David, Lauchringen (DE); Martin Engelhardt, München (DE); Jörg Freudenberger, Kalchreuth (DE); Eckhard Hempel, Fürth (DE); Martin Hoheisel, Erlangen (DE); Thomas Mertelmeier, Erlangen (DE); Franz Pfeiffer, Brugg (CH); Stefan Popescu, Erlangen (DE); Manfred Schuster, München (DE)

(73) Assignee: Siemens Aktiengesellschaft, Munich (DE)

( * ) Notice: Subject to any disclaimer, the term of this patent is extended or adjusted under 35 U.S.C. 154(b) by 140 days.

(21) Appl. No.: 12/159,486

(22) PCT Filed: Dec. 6, 2006

(86) PCT No.: PCT/EP2006/069355

§ 371 (c)(1),
(2), (4) Date: Nov. 25, 2008

(87) PCT Pub. No.: WO2007/074029

PCT Pub. Date: Jul. 5, 2007

(65) Prior Publication Data

US 2009/0154640 A1    Jun. 18, 2009

(30) Foreign Application Priority Data

Dec. 27, 2005  (DE)  ........................ 10 2005 062 447
Dec. 27, 2005  (DE)  ........................ 10 2005 062 448
Feb. 1, 2006   (DE)  ........................ 10 2006 004 604
Feb. 1, 2006   (DE)  ........................ 10 2006 004 976
Aug. 9, 2006   (EP)  ................................ 06016644

(51) Int. Cl.
*G01N 23/04* (2006.01)
(52) U.S. Cl. .......................................... 378/62; 378/36
(58) Field of Classification Search .................. 378/36, 378/62, 82
See application file for complete search history.

(56) References Cited

U.S. PATENT DOCUMENTS 4,057,745 A   11/1977   Albert
4,723,263 A    2/1988   Birnbach et al.

(Continued)

FOREIGN PATENT DOCUMENTS

EP    1 447 046    8/2004

(Continued)

OTHER PUBLICATIONS

"Phase-Contrast Imaging Using Polychromatic Hard X-rays," Wilkins et al., Nature, 384(1996) pp. 335-338; Nature, 384 (1996) pp. 335-336.

(Continued)

*Primary Examiner*—Chih-Cheng G Kao
(74) *Attorney, Agent, or Firm*—Schiff Hardin LLP

(57) ABSTRACT

In a focus detector arrangement and method for an x-ray apparatus for generating projection or tomographic phase-contrast images of an examination subject, a beam of coherent x-rays is generated by an anode that has areas of different radiation emission characteristics arranged in bands thereon, that proceed parallel to grid lines of a phase grid that is used to generate the phase-contrast images.

39 Claims, 4 Drawing Sheets

U.S. PATENT DOCUMENTS

| | | | |
|---|---|---|---|
| 5,745,546 | A | 4/1998 | Hell et al. |
| 5,812,629 | A | 9/1998 | Clauser |
| 7,180,979 | B2 | 2/2007 | Momose |
| 7,433,444 | B2 | 10/2008 | Baumann et al. |
| 2001/0046276 | A1* | 11/2001 | Schneider et al. ............. 378/58 |
| 2007/0153979 | A1* | 7/2007 | Baumann et al. ............ 378/138 |
| 2007/0189449 | A1 | 8/2007 | Baumann et al. |

FOREIGN PATENT DOCUMENTS

WO     WO 2004/058070     7/2004

OTHER PUBLICATIONS

"An X-ray Interferometer," Bonse et al., Applied Physics Letters, vol. 6, No. 8, Apr. 15, 1965, pp. 155-156 NY, USA; 6; Magazine; 1965.

"X-ray Plane-Wave Topography Observation of the Phase Contrast from a Non-Crystalline Object," X-ray Laboratory, Russia, J. Phys. D. Appl. Phys. vol. 28, 1995, pp. 2314-2317, Russia IOP Publishing, Ltd.; 28; 0022-3727/95; Magazine; 1995.

Phase-Sensitive X-ray Imaging, Fitzgerald, Physics Today, Vo. 53, Jul. 2000, pp. 23-26; American Institute of Physics; 53 Magazine; 2000.

"Diffraction Enhanced X-ray Imaging," Chapman, Phys. Med. Biol. vol. 42, 1997 pp. 2015-2025; IOP Publishing Ltd. 42; 0031-9155/97 Magazine 1997.

Phase Retrieval and Differential Phase-Contrast Imaging with Low Brilliance X-ray Sources, Pfeiffer et al., Nature Physics 265, 2006 Published On-line Mar. 26, 2006; Nature Publishing Group, 165; Magazine; 2006.

"X-ray Phase Imaging with a Grating Interferometer," Weitkamp et al., Optics Express, 2005.

"X-ray Talbot Interferometry for Medical Phase Imaging," Momose, AIP Conference Proceedings, vol. 716 pp. 156-159 2004.

"Hard X-ray Phase Imaging and Tomography with a Grating Interferometer," Weitkamp et al., Proceedings of the SPIE, vol. 5535, pp. 137-142 (2004).

X-ray Data Booklet; Vaughn,. (ed) Lawrence Berkeley Laboratory, Berkeley, 1986 pp. 2-28-2-29 (1986).

* cited by examiner

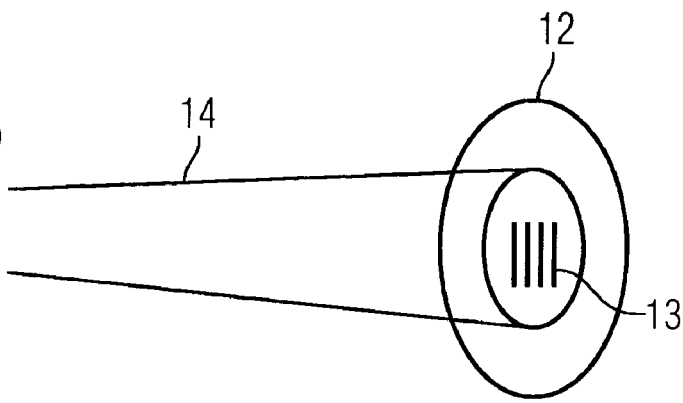
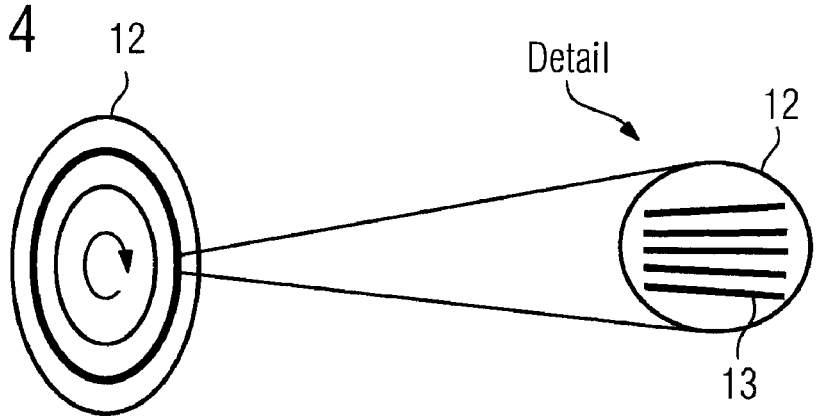
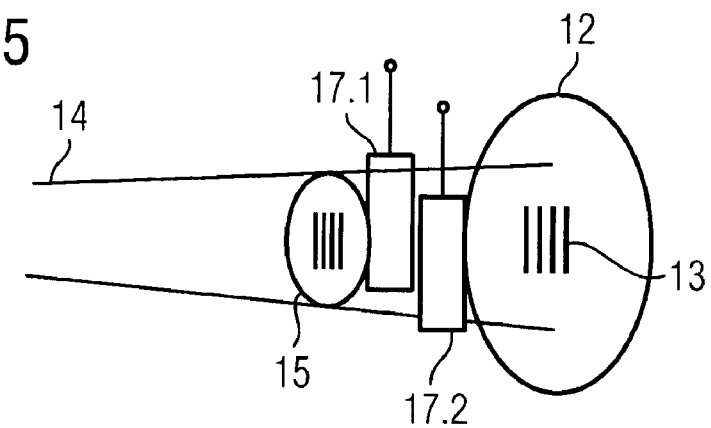

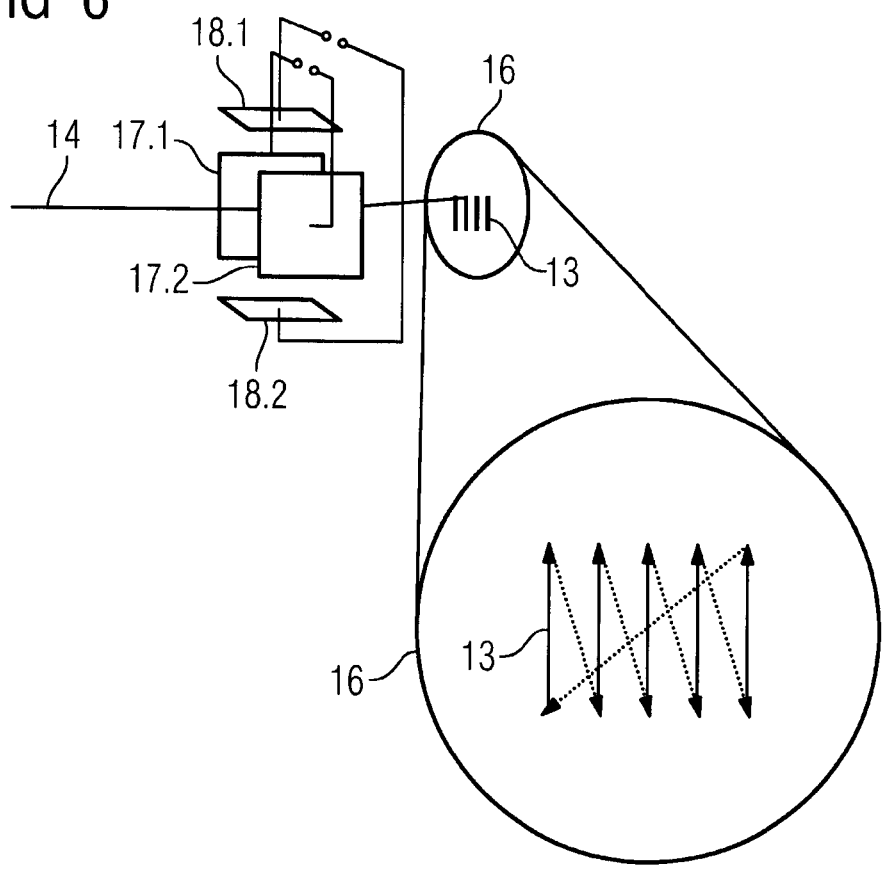
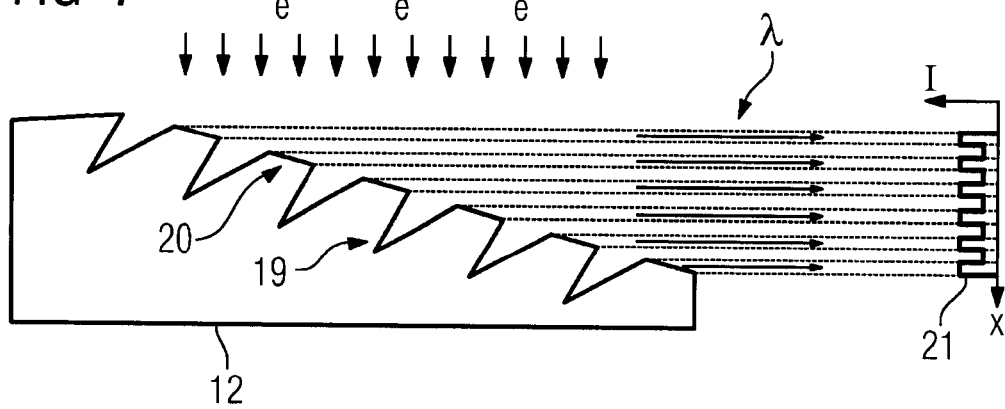

FOCUS DETECTOR ARRANGEMENT AND METHOD FOR GENERATING CONTRAST X-RAY IMAGES

BACKGROUND OF THE INVENTION

1. Field of the Invention

The present invention concerns a focus detector arrangement of an x-ray apparatus for generation of projection or tomographic phase contrast exposures of an examination subject: of the type having a radiation source arranged on a first side of the examination subject, that generates a beam of coherent rays with grid-like origin, a phase grid arranged in the beam path on the opposite second side of the examination subject that generates an interference pattern of the x-ray radiation in a predetermined energy range of the x-ray radiation, and an analysis detector system that locally detects at least one interference pattern generated by the phase grid relative to its phase shift. The invention also concerns a method for generation of projection or tomographical x-ray phase contrast exposures with such a focus detector arrangement.

2. Description of the Prior Art and Related Subject Matter

Focus detector arrangements for generation of projection or tomographic phase contrast exposures of an examination subject or of the type and such methods are generally known. EP 1 447 046 A1 and German patent applications 10 2006 017 290.6, 10 2006 015 358.8, 10 2006 017 219.4, 10 2006 015 356.1 and 10 2006 015 355.3 are examples.

In principle two effects that occur upon passage of the radiation through matter, namely an absorption and a phase shift of the radiation passing through an examination subject, can be considered for imaging with ionizing radiation (in particular with x-rays). It is also known that the effect of the phase shifts upon passage of a beam through an examination subject reacts significantly more strongly than the absorption effects to smaller differences in the composition of the penetrated matter.

The phase shift caused by the subject must be evaluated for such a phase contrast radiography or phase contrast tomography. Both projection images of the phase shift or even a number of projection images of tomographical depictions of the phase shift that is caused by a volume element can be calculated, analogous to x-ray radiography and x-ray tomography.

Such phase shifts for generation of projection or tomographic exposures can be measured by the use of interferometric grids. The previously cited documents are likewise referenced with regard to these interferometric methods. In these methods an examination subject is irradiated by a coherent x-ray beam that is subsequently directed through a grid with a period adapted to the wavelengths of the radiation, so an interference pattern arises that is dependent on the occurred radiation shift. This interference pattern is measured by a subsequent analysis-detector arrangement so that the phase shift can be determined.

The method described above requires a sufficient degree of spatial coherence in the employed radiation. This can be achieved by an extremely small focus, for example, but the achievable dose rating is barely usable for medical applications due to the long required exposure time. Another possibility is the use of synchrotron radiation. Such applications are much too complicated in practice. Finally, in the cited prior art it is also proposed to use a focus with a conventional large focal spot as is known in the field of computed tomography and to arrange what is known as a source grid between the focus and the examination subject. The slits of this source grid generate a field of individual coherent rays of a specific energy having dose rating that is sufficient to generate the known interference pattern, with the use of a phase grid arranged after the subject in the beam direction.

In this manner it is possible to use radiation sources that have dimensions that correspond to normal x-ray tubes in CT systems and transmission x-ray systems, such that easily differentiated soft tissue exposures can now also be made with the use of x-ray apparatuses in the field of general medical diagnostics, for example.

One problem given this type of focus detector combination is that, given the use of such source grids, a relatively high dose proportion nevertheless occurs that acts as quasi-coherent radiation, and therefore produces a high background noise and also leads to unnecessary radiation exposure of the examined patient.

SUMMARY OF THE INVENTION

An object of the present invention is to provide a focus detector arrangement that achieves an improved dose utilization for phase contrast imaging with dose rating that is sufficient for medical purposes. The ratio of radiation usable for phase contrast measurement to radiation that is usable only for absorption measurements should thus also be improved.

The invention is based on the insight that it is possible to also achieve the effect of the generation of a beam of quasi-coherent rays with grid-like origin by the use of a source grid directly on an anode, due to regions arranged in bands being generated that exhibit a different radiation emission. A movement of the source grid thus can also advantageously be simulated.

The above object is achieved in accordance with the present invention by a focus detector arrangement for an x-ray apparatus for generating projection and tomographic phase contrast exposures of an examination subject, wherein a radiation source is located on a first side of the examination subject that generates a beam of coherent x-rays with a grid-like origin, a phase grid in the beam path of the x-rays on the opposite, second side of the examination subject, the phase grid diffracting adjacent coherent x-rays and thus generating an interference pattern (standing wave field) of the x-ray radiation in a specific energy range of the x-ray radiation, dependent on the phase shift produced by tissue of the examination subject, an analysis-detector system that detects the interference pattern generated by the phase grid relative to the local intensity distribution thereof, in order to determine a local phase shift, and wherein the beam of coherent x-rays with grid-like origin is generated by an anode that has regions of different radiation emission formed as bands that proceed parallel to the grid lines of the phase grid.

In a first embodiment of the focus detector arrangement, at least the surface of the anode in the region of an electron beam focal spot generated for operation of the x-ray tube has regions of different materials arranged in bands.

A unit that shifts the anode (advantageously perpendicular to the longitudinal direction of the bands) can be provided, that shifts to displace the regions arranged in bands substantially perpendicularly to the longitudinal direction of the bands.

Alternatively, an electron mask with band-like apertures between cathode and anode, which band-like apertures are reproduced on the anode and thereby lead to band-like regions of different radiation emission on the anode. At least one optoelectronic lens can additionally be arranged between the electron mask and the anode and/or between cathode and electron mask.

The optoelectronic lens can be fashioned as a magnetic field lens or as an electrical field lens.

According to the invention, a unit is provided that shifts the electron mask, advantageously shifting it perpendicularly to the longitudinal direction of the bands.

A unit can be provided that adjusts at least one optoelectronic lens which cause a displacement of the mask reproduction on the anode, advantageously perpendicular to the longitudinal direction of the bands.

In a further embodiment, the anode has lands and grooves arranged in bands, at least in the region of an electron beam focal spot generated for operation of the x-ray tube, that cause shadows to arise or, due to the forming field lines formed, the electrons preferably strike the lands on the anode and preferably produce x-ray radiation at those locations.

The surface of the lands and grooves can be wave-shaped (advantageously sinusoidal), for example, or sawtooth-shaped, trapezoidal or rectangular.

Moreover, the anode is preferably executed as a rotary anode, due to the better cooling thereof. Depending on the requirements, the rotary anode can have bands directed in the rotation direction, bands on a conical envelope surface of the rotary anode, or bands on a cylindrical envelope surface of the rotary anode.

Furthermore, in an embodiment of the focus detector arrangement the bands of the rotary anode can exhibit a directional component axial to the rotation axis of the rotary anode, and a pulse generator is provided to generate and control a stroboscopic pulsation of the tube current. A matching unit can hereby be provided to match the frequency and the phase of the pulsation of the tube current and the rotation speed so that the position of the bands of different materials in the maximum of the tube current remains unchanged relative to the x-ray tube.

The matching unit can also be fashioned such that the position of the bands of different materials in the maximum of the tube current migrates (advantageously in steps) relative to the x-ray tube in the rotation direction for measurement of the phase shift given stationary phase grid and stationary analysis grid. The known movement of the source grid is thereby simulated.

In principle the bands in this focus detector arrangement should be arranged parallel to the grid lines of the phase grid.

However, the bands can also exhibit an angle (advantageously 45°) relative to the radial direction.

In a further embodiment of the focus detector arrangement according to the invention, the x-ray tube has a unit for generation and deflection of a clustered electron beam, so the electron beam is moved along at least one imaginary grid line on an anode surface.

In another embodiment, multiple grid lines can be provided and the electron beam can jump from grid line to grid line. The grid lines can exhibit intervals among one another that represent an integer multiple of a basic interval. The periodicity of the grid is hereby preserved, but at the same time different intervals are enabled. However, a periodic grid in which all grid lines run in parallel with the same interval can be viewed as a simplest version of this embodiment, with the electron beam scanning the grid lines in succession or in an arbitrary order.

A rotary anode preferably is used here for better heat dissipation.

In a preferred embodiment, this rotary anode can have a conical anode surface, with the lines on this surface being directed radially or tangentially relative to the rotation axis of the rotary anode.

In a further version of this embodiment with clustered and directed electron beam, the rotary anode can have a cylindrical anode surface, with the lines on this surface being directed parallel or perpendicular to the rotation axis. It is also possible to align the lines at an angle relative to the rotation axis and to the radial direction.

In version the scan period (thus the period of one revolution of the rotary anode) of the electron beam is small (factor of ½-1/10), advantageously is very small (factor of <1/10) relative to the scan period of the detector in the analysis-detector system.

Moreover, the unit for deflection of the electron beam can be designed such that the movement of a source grid is simulated to determine the phase shift.

The focus detector arrangements described above can be used for generation of projection phase contrast exposures in an x-ray system, for generation of projective or tomographical phase contrast exposures in an x-ray C-arm system or for generation of tomographical phase contrast exposures in an x-ray CT system, for example.

The above object also is achieved by a method for generation of projective or tomographical x-ray phase contrast exposures of an examination subject with the use of a focus detector arrangement having an x-ray radiation source, a phase grid, and an analysis-detector system, in which a beam of coherent rays is generated with grid-like origin by an anode which has regions with different radiation emission arranged in bands that run parallel to the grid lines of the phase grid.

For example, the bands of different radiation emission can be generated by regions of different materials arranged in bands.

The bands of different radiation emission can also be generated via regions of different elevation and depth arranged in bands.

A rotary anode can be used in order to effect a better heat dissipation and/or to simulate the movement of the replaced source grid, wherein the bands of the rotary anode are advantageously operated with an axial direction component relative to the rotation axis of the rotary anode and the tube current is stroboscopically pulsed. The frequency and phase of the pulsation of the tube current at the rotation frequency of the rotary anode can thus thereby be selectively matched to one another such that the position of the bands of different radiation emission remains in the maximum of the tube current relative to the x-ray tube, or such that the movement of a source grid is simulated to determine the phase shift.

In another embodiment of the method according to the invention, an electron beam is moved on the anode surface corresponding to the grid lines of an x-ray-optical source grid to generate a beam of coherent rays, wherein the grid lines of the simulated source grid remain stationary.

Moreover, the an electron beam can be moved on the anode surface corresponding to the grid lines of an x-ray-optical source grid to generate a beam of coherent rays, so the movement of the grid lines of the simulated source grid is simulated to determine the phase shift.

In all described embodiment variants, the curve of bands forming intensity maxima can be aligned parallel, tangential or at an angle relative to the rotation axis.

BRIEF DESCRIPTION OF THE DRAWINGS

FIG. 3 illustrates an embodiment of an anode with material bands composed of material with different Z relative to the anode base material, in accordance with the present invention.

FIG. 4 illustrates an embodiment of a rotary anode with radially aligned material bands composed of material with different Z relative to the anode base material, in accordance with the present invention.

FIG. 5 shows an embodiment of an anode with an electron beam that is selectively directed by an electron mask.

FIG. 6 shows an embodiment of an anode with a clustered electron beam and a controlled beam deflection device.

FIG. 7 shows an embodiment of the anode in accordance with the present invention having notches.

DESCRIPTION OF THE PREFERRED EMBODIMENTS

Figure 1:
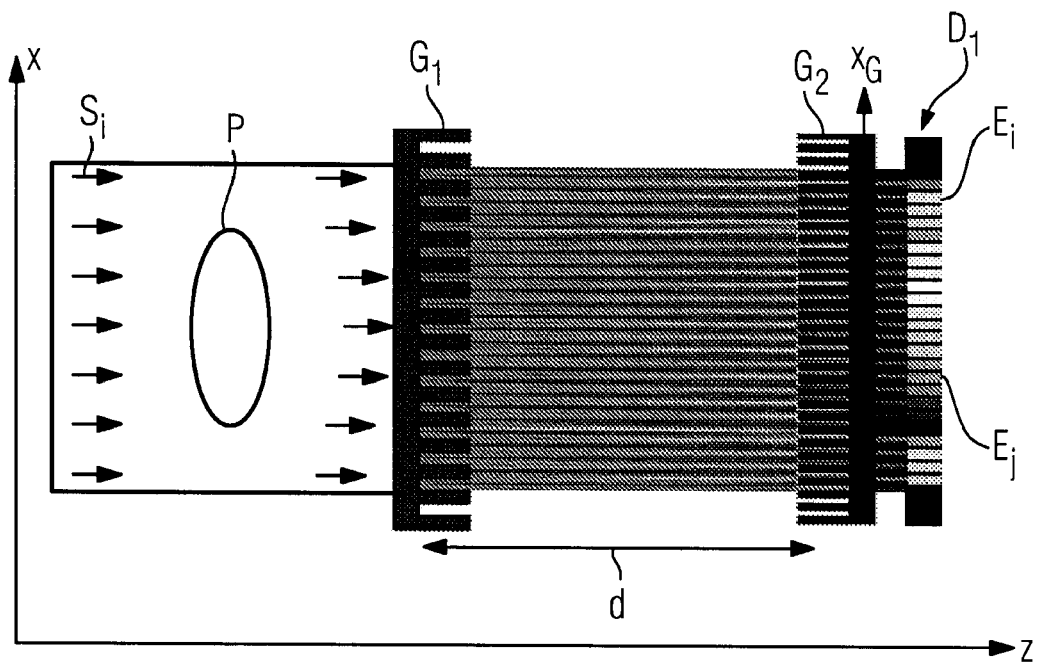
FIG. 1 shows a longitudinal section through a schematic illustration of a focus detector arrangement with a phase grid, an analysis grid and a detector to detect the interference pattern.
Figure 2:
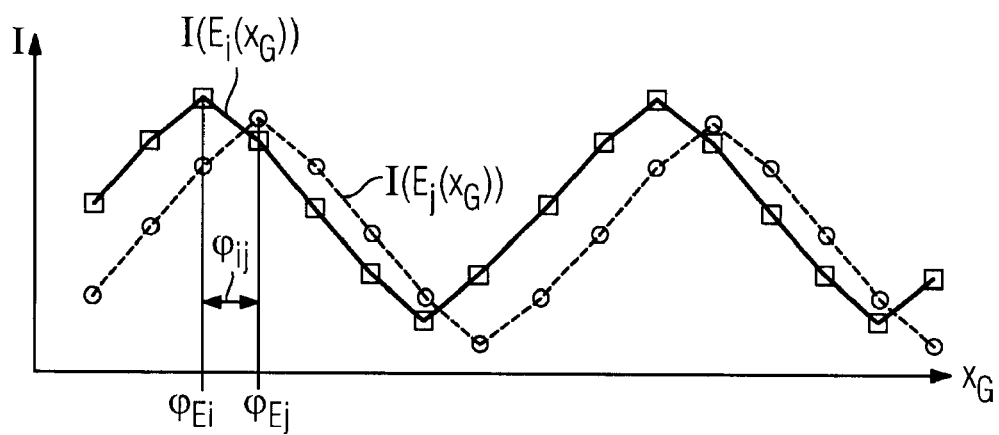
FIG. 2 shows an intensity curve for selected detector elements that occurs upon relative displacement of the grid.

FIG. 1 shows a quasi-coherent radiation coming from a focus or individual coherent rays coming from a source grid that penetrate a probe P, wherein phase shift appearances of the probe P occur after the penetration. An interference pattern which is represented by the grey shading is hereby generated upon passage through the grid $G_1$, which interference pattern (with the aid of the grid $G_2$) leads to different radiation intensities per detector element on the subsequent detector $D_1$ and its detector elements, wherein what is known as a Moiré pattern forms at what is known as a Talbot distance. If one considers the detector element $E_1$ dependent on an offset $x_G$ of the analysis grid $G_2$ and translates the intensity $I(E_i(x_G))$ as a function of the offset $x_G$ over intensity I, one obtains a sinusoidal rise and fall (shown in FIG. 2) of the intensity I at this detector element $E_i$. If these measured radiation intensities I for each detector element $E_i$ or $E_j$ are plotted dependent on the offset $x_G$, the functions $I(E_i(x_G))$ and $I(E_j(x_G))$ approximately cancel for the various detector elements that ultimately establish the spatial position of the x-ray beam between the focus and the respective detector element. The phase shift $\phi$ and the relative phase shift $\phi_{ij}$ between the detector elements can be determined from the functions.

For each ray in space, the phase shift per ray can thus be determined via at least three measurements with respective offset analysis grid, from which the pixel values of a projective exposure can be calculated directly (in the case of projective x-ray exposures) or projections whose pixel values correspond to the phase shift can be created (in the case of a CT examination), such that which volume element in the examination subject is to be assigned to which portion of the measured phase shift can be calculated from this with the aid of known reconstruction methods. Slice images or volume data that reflect the local effect of the examined subject with regard to the phase shift of an x-ray beam can therefore be calculated from this. Since slight differences in the composition already exert a strong effect on the phase shift, very high-detail and high-contrast volume data of relatively similar materials (in particular of soft tissue) can be achieved.

This variant of the detection of phase shifts of the x-rays that penetrate an examination subject with the aid of a repeatedly offset analysis grid and measurement of the radiation intensity on a detector element after the analysis grid requires that at least three measurements of each x-ray beam must be implemented with respectively displaced analysis grid.

In principle, the possibility also exists to forego such an analysis grid and instead to use a sufficiently finely structured detector. In this case fewer dose losses occur in the measurement and the phase shift in the observed beam can be determined with a single measurement.

It is necessary to use coherent radiation to measure the phase contrast. According to the invention, for this a field (array) of individual coherent radiation is generated not by a source grid behind a planar focus but rather by a grid-like design of the electron beam focal spot on the anode to simulate such a grid.

This array of sources that are individually coherent but incoherent relative to one another can be produced in that a corresponding intensity distribution of the x-rays emitted by the x-ray tube is generated. This can be achieved in the various ways:

A first possible embodiment is shown in FIG. 3, in which a relatively broad electron beam 14 is directed at an anode base plate 12. The anode base plate 12 consists of a material with low Z-value which should preferably exhibit high heat conductivity, high melting point, good stability and sufficient electrical conductivity. For example, aluminum, beryllium or diamond can be used here. Given diamond the electrical conductivity can, for example, be achieved in that the material is doped or is coated with a conductive layer. A material with high Z-value (for example copper, molybdenum or tungsten) should be present at the band-shaped regions 13 where x-rays should preferably be emitted. The bands 13 produced from a material with high Z-value consequently emit x-rays with relatively high intensity. Via a suitable selection of the material corresponding to the present acceleration voltage, in particular the characteristic lines of the material can be emitted while the surrounding material advantageously exhibits no characteristic lines in this range. It should be noted that this material also emits characteristic x-ray radiation; however, its energy is relatively low and is largely already absorbed by the tube window. Moreover, the effectiveness of the generation of braking radiation is lower since this proportional to the Z-value. Although x-rays are likewise generated in regions in which the anode base plate is struck by the electron beam, overall it is with significantly lower intensity than in the band-shaped regions with high Z-value.

An x-ray tube with rotating anode can also advantageously be used that delivers a higher heat capacity for a higher x-ray flux. In this case many radially oriented bands can be distributed along an entire circular track. An example of this is presented in FIG. 4.

Given continuous x-ray emission, however, the elementary sources in this arrangement continuously shift relative to the interferometer grid due to the anode rotation. This effect can on the one hand be utilized in order to simulate a moving source grid for phase determination; on the other hand, however, this effect can also be avoided in that the electron beam (and therefore also the x-ray emission) is pulsed synchronously with the anode rotation such that its maximum is always reached when the bands have migrated further by one period. Due to a stroboscopic effect, the position of the elementary x-ray emitter then appears to be static given an observation from the detector.

A source shift (required for the phase decomposition) that differs from the rotation speed of the anode can additionally be implemented via adjustment of the phase between pulsation and rotation.

In a further embodiment variant it is proposed to trim a portion of the electron beam 14 striking the anode plate 16 using an electron mask 15 as it is drawn in FIG. 5. The electron mask 15 can be connected with a specific potential (voltage). This voltage should thereby be low enough to prevent that the striking electrons already achieve a kinetic energy that is too high, whereby the temperature of the electron mask would rise too severely and additional, unwanted secondary x-ray radiation would be generated. This can be avoided in that, for example, the electron mask is charged with a voltage below the energy at which the interferometer assembly is set.

This electron mask can additionally be used as a focusing electrode which focuses the generated electrons onto the anode surface. For this the mask can also be connected to a well-defined control voltage (focusing voltage). In this improved arrangement the electron mask blocks no electrons; rather concentrates the exiting electron beam into multiple strongly focused sub-beams. The efficiency is significantly improved.

According to a continuative, different or, respectively, expansive embodiment of the focus detector arrangement, the electron beam striking the anode can be correspondingly deflected using an electrical field (generated by the optional electrode plates 17.1 and 17.2) or a magnetic field, thus an electron optic. The electron beam can additionally be switched on and off via such an arrangement.

Such an arrangement is shown by way of example and severely schematized in FIG. 6 for the case of an electrostatic optic. In FIG. 6 a clustered electron beam 14 is presented that is controlled by two plate electrode pairs 17.1, 17.2 and 18.1, 18.2 acting perpendicular to one another with regard to its deflection in its direction. Through a corresponding control of the plate electrode pairs, the electron beam can "scan" the anode in lines (similar to the scanning of a television image) with the desired interval of the lines and thereby generate the desired x-ray radiation. If a snapshot is considered, in principle only a point focus is hereby generated, however a band pattern that consists of at least one or more bands corresponding to the lines of a source grid is generated averaged over longer radiation time. The function of a source grid is thus also hereby achieved averaged over time.

The pulsation of the electron beam can occur, for example by a targeted periodic variation of the cathode temperature, fast and significant deflection of the electron beam, field emission cathodes, electrically controllable electron emission, photoemission cathodes, cathodes with light- or laser-induced emission, streak tubes, gated electron tubes such as a triode or pentode, or by traveling wave tubes.

Alternatively, a linear focus and only an individual axis deflection perpendicular to this can be applied. Given this approach the hotspot temperature is distributed along the linear focus. As already mentioned, here as well a source displacement possible for the phase decomposition (or, respectively, required in the event that no movable grids or detectors are used) can be attained via the horizontal deflection means.

A further possibility for improvement exists in the use of an x-ray tube with rotating anode, optionally with electron beam deflection. In this arrangement the hotspot temperature is distributed long a longer circular track. The rotation with sufficient speed smears the thermal load homogeneously over the track of the electron beam.

Furthermore, it should be noted that the maximum irradiation of an x-ray tube is limited by the dissipation of the heat generated at the focal spot. If an x-ray source consisting of multiple bands corresponding to the embodiment variants according to the invention presented above is used, an improved heat dissipation on the anode surface results. In contrast to an arrangement that consists of a planar focal spot and source grid, no or less heat is produced at the regions between the bands, such that a higher brilliance of the radiation can therefore be achieved.

With regard to the previously described arrangement with an anode made from different materials that are arranged in bands, the situation arises that although nearly the same heat flow id generated in the bands and in the region between the bands, the material between the bands exhibits a lower Z-value, and therefore a significantly greater penetration depth of the electrons is present, such that the heat flow also reaches deeper and therefore an improved heat dissipation is present.

It is also advantageous that no mechanical devices are necessary for "virtual" movement of the "grid"; rather, this can be electronically generated in a simple manner and very precisely, quickly and without mechanical wear.

Figure 8:
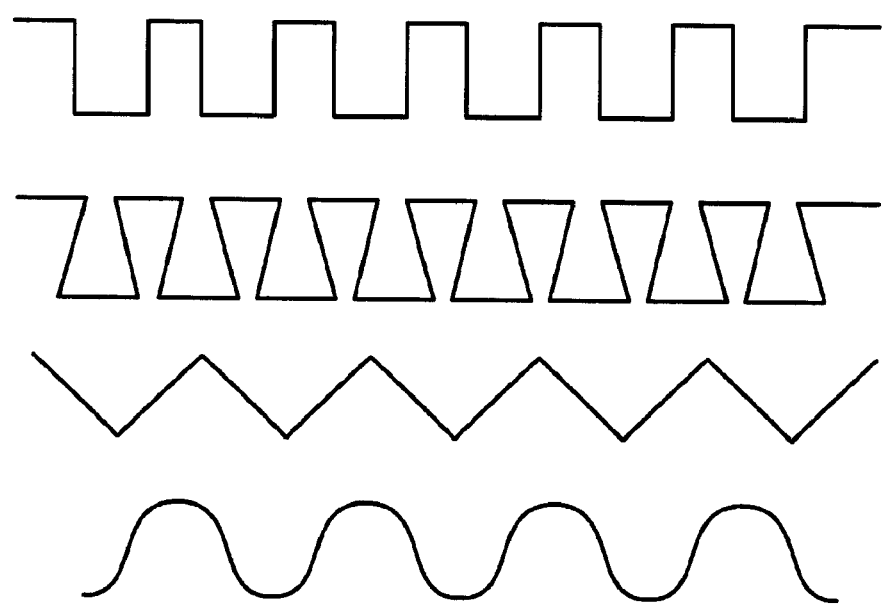
FIG. 8 shows an embodiment of the notches in the anode material in cross-section.

Another embodiment of an anode 12 according to the invention is presented in FIG. 7. This has notches 19 which shade the anode material with regard to the incoming electrons e⁻ while the electrons e⁻ increasingly strike the plateaus 20 of the anode. Band-shaped regions with increased and reduced source intensity of generated braking and x-ray radiation λ correspondingly arise on the anode surface. The source intensity Q of the x-ray radiation relative to an arbitrary x-axis is schematically plotted to the right as a stepped line 21. It is noted that other embodiments (for example groove-shaped depressions or even a wave-shaped or sinusoidal surface curve) are also possible. It is hereby essential only that x-ray radiation with sufficient intensity arise on the anode surface. Four examples of other possible surface curves are shown in cross-section in FIG. 8.

Figure 9:
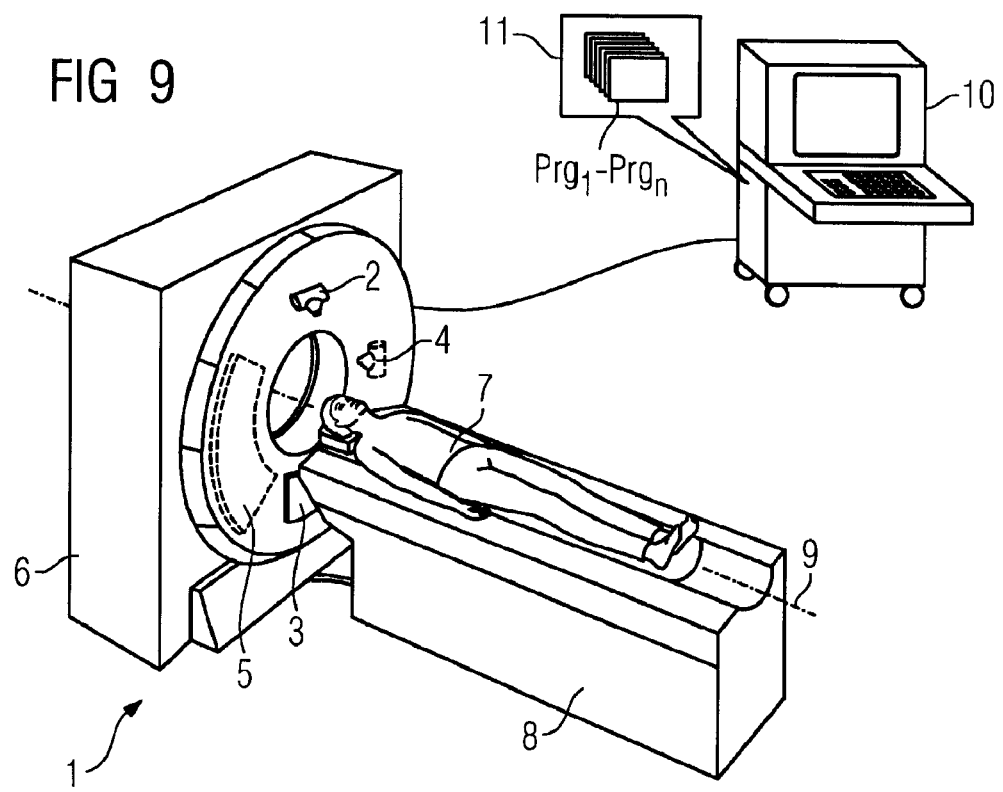
FIG. 9 schematically illustrates an x-ray computed tomography (CT) system embodying a focus detector system according to the present invention.

A complete computer CT system for use of the focus detector system according to the invention or, respectively, implementation of the method according to the invention is presented in FIG. 9. This shows the CT system 1 that has a first focus detector system with an x-ray tube 2 and an oppositely situated detector 3 that are arranged on a gantry (not shown in detail) in a gantry housing 6. The x-ray tube 2 has a multi-band focus according to the invention which generates quasi-coherent x-rays. Furthermore, an x-ray-optical grid system (as is shown in FIG. 1, for example) is arranged in the beam path of the first focus detector system, such that the patient 7 who is located on a patient bed 8 that can be displaced along the system axis 9 can be shifted into the beam path of the focus detector system and scanned there. The phase shift of the passing x-rays is hereby measured and the spatial distribution of the index of refraction is determined via known reconstruction methods. The control of the CT system is implemented via a computation and control unit 10 in which programs $Prg_1$ through $Prg_n$ are stored that, in operation, implement the method described in the preceding and also control the x-ray tube according to the invention with its multi-band focus and reconstruct corresponding tomographical images from the measured beam-dependent phase shifts.

Instead of the single focus detector system, a second focus detector system can optionally be arranged in the gantry housing. This is indicated in FIG. 9 by the x-ray tube 4 (shown in dashes) and the detector 5 (shown in dashes).

It should additionally be noted that not only phase shifts of the x-ray radiation can be measured with the shown focus detector systems; rather, these are furthermore also suitable for conventional measurement of the radiation absorption and reconstruction of corresponding absorption exposures. Combined absorption and phase contrast exposures can also be generated if applicable.

Although modifications and changes may be suggested by those skilled in the art, it is the intention of the inventors to embody within the patent warranted heron all changes and modifications as reasonably and properly come within the scope of their contribution to the art.

We claim as our invention:

1. A focus detector arrangement for an x-ray apparatus for generating projection or tomographic phase contrast exposures of an examination subject, comprising:
   a radiation source located at a first side of the examination subject, that generates a beam of coherent x-ray radiation with a grid-like origin;
   a phase grid located in a path of said beam at an opposite, second side of the examination subject, said phase grid comprising spaced-apart grid lines that diffract adjacent coherent rays in said beam to generate an interference pattern of the x-ray radiation in a predetermined energy range of the x-ray radiation dependent on a phase shift of the x-ray beam produced by tissue of the examination subject;
   an analysis-detector system that detects at least said interference pattern generated by said phase grid relative to a local intensity distribution thereof, to determine a local phase shift; and
   said radiation source comprising an anode from which said beam of coherent x-ray radiation with a grid-like origin is emitted, said anode comprising regions with respectively different radiation emission characteristics proceeding in spaced-apart bands that are parallel to the grid lines of the phase grid.

2. A focus detector arrangement as claimed in claim 1 wherein said x-ray source comprises an electron beam emitter that emits an electron beam onto a focal spot of the anode, from which said x-ray radiation is emitted, and wherein said bands at said anode are located in said focal spot, said anode being comprised of anode base material and said bands being comprised of a material different from said anode base material.

3. A focus detector arrangement as claimed in claim 2 comprising a displacement unit configured to interact with the anode to shift the anode perpendicular to a longitudinal direction of said bands.

4. A focus detector arrangement as claimed in claim 2 comprising a displacement unit that interacts with said bands to shift said band perpendicular to a longitudinal direction of the bands.

5. A focus detector arrangement as claimed in claim 1 wherein said x-ray source comprises a cathode that emits an electron beam that strikes the anode at a focal spot from which said beam of coherent x-ray radiation with a grid-like origin is emitted, and an electron mask between the cathode and the anode having band-like apertures through which said electron beam passes to produce said bands on said anode in said focal spot.

6. A focus detector arrangement as claimed in claim 5 wherein said x-ray source comprises at least one opto-electronic lens located in a path of said electron beam at a location selected from the group consisting of between said electron mask and said anode and between said cathode and said electron mask, said at least one opto-electronic lens being a lens selected from the group consisting of magnetic field lenses and electrical field lenses.

7. A focus detector arrangement as claimed in claim 6 comprising an adjustment unit configured to interact with said at least one opto-electronic lens to cause a shift of the bands produced by said electron mask in said focal spot perpendicular to a longitudinal direction of the bands.

8. A focus detector arrangement as claimed in claim 5 comprising a displacement unit configured to interact with said electron mask to shift said electron mask perpendicularly to a longitudinal direction of said bands.

9. A focus detector arrangement as claimed in claim 1 wherein said x-ray source comprises an electron source that emits an electron beam that strikes said anode at a focal spot, and wherein said anode comprises a plurality of adjacent, alternating lands and grooves forming said bands, located in said focal spot.

10. A focus detector arrangement as claimed in claim 9 wherein said lands and grooves exhibit a surface profile at a surface of the anode at which said focal spot is located, said surface profile being selected from the group consisting of sinusoidal profiles, sawtooth profiles, trapezoidal profiles, and rectangular profiles.

11. A focus detector arrangement as claimed in claim 1 wherein said anode is rotatably mounted in said x-ray source, forming a rotary anode.

12. A focus detector arrangement as claimed in claim 11 wherein said rotary anode rotates in a rotation direction, and wherein said bands are aligned relative to said rotation direction.

13. A focus detector arrangement as claimed in claim 12 wherein said rotary anode comprises an envelope surface on which said bands are located, said envelope surface being selected from the group consisting of a conical envelope surface and a cylindrical envelope surface.

14. A focus detector arrangement as claimed in claim 12 wherein said bands are aligned relative to said rotation direction so as to exhibit a directional component that is axial to a rotation axis of the rotary anode, and wherein said x-ray source is an x-ray tube operated with a tube current, and comprising a control unit that generates and controls a stroboscopic pulsation of said tube current.

15. A focus detector arrangement as claimed in claim 14 wherein said control unit is configured to match a frequency and phase of the pulsation of the tube current to a rotation speed of the rotary anode to maintain a substantially constant position of said bands coinciding with a maximum of said tube current.

16. A focus detector arrangement as claimed in claim 14 wherein said control unit is configured to match a frequency and phase of said pulsation of the tube current to a rotation speed of said rotary anode to cause a position of said bands coinciding with a maximum of said tube current to migrate in steps in said rotation direction, for measurement of said phase shift with a stationary phase grid and a stationary analysis grid.

17. A focus detector arrangement as claimed in claim 1 wherein said anode is rotatably mounted in said x-ray source, forming a rotary anode, and wherein said bands are at a non-zero angle relative to a radial direction of said rotary anode.

18. A focus detector arrangement as claimed in claim 1 wherein said x-ray source is an x-ray tube comprising an electron source that emits an electron beam that strikes said anode to cause said anode to emit said x-ray radiation with a grid-like origin, and a deflection unit located in a path of said electron beam configured to interact with the electron beam to cause the electron beam to move along at least one imaginary grid line on a surface of said anode.

19. A focus detector arrangement as claimed in claim 18 wherein said deflection unit is configured to cause said electron beam to move along multiple imaginary grid lines on said surface of said anode, by jumping from grid line-to-gridline.

20. A focus detector arrangement as claimed in claim 19 wherein said control unit is configured to move said electron beam along multiple grid lines with respective spacings therebetween that are integer multiples of a basic spacings.

21. A focus detector arrangement as claimed in claim 18 wherein said anode is rotatably mounted in said x-ray source, forming a rotary anode.

22. A focus detector arrangement as claimed in claim 21 wherein said deflection unit is configured to cause said electron beam to move along multiple imaginary grid lines on said surface of said anode, by jumping from grid line-to-grid line, and wherein said rotary anode has a conical anode surface on which said electron beam is moved along said multiple grid lines, with said grid lines oriented in an alignment relative to a rotation axis of the rotary anode selected from the group consisting of radial alignment and tangential alignment.

23. A focus detector arrangement as claimed in claim 21 wherein said deflection unit is configured to cause said electron beam to move along multiple imaginary grid lines on said surface of said anode, by jumping from grid line-to-grid line, and wherein said rotary anode has a cylindrical anode surface on which said electron beam is moved along said multiple grid lines, with said grid lines being oriented on said cylindrical surface in an alignment relative to a rotation axis of the rotary anode, selected from the group consisting of parallel to the rotation axis and perpendicular to the rotation axis.

24. A focus detector arrangement as claimed in claim 21 wherein said deflection unit is configured to cause said electron beam to move along multiple imaginary grid lines on said surface of said anode, by jumping from grid line-to-grid line, parallel with said grid lines being aligned at a non-zero angle relative to a rotation axis of the rotary anode and relative to a radial direction of the rotary anode.

25. A focus detector arrangement as claimed in claim 21 wherein said deflection unit is configured to cause said electron beam to move along multiple imaginary grid lines on said surface of said anode, by jumping from grid line-to-grid line and wherein said analysis-detector system detects said interference pattern with a scan period, and wherein said deflection unit deflects said electron beam over all of said multiple grid lines with a scan period that is less than half of said scan period of said analysis-detector system.

26. A focus detector arrangement as claimed in claim 25 wherein said scan period of said electron beam is less than one-tenth of said scan period of said analysis-detector system.

27. A focus detector arrangement as claimed in claim 18 wherein said deflection unit is configured to cause said electron beam to move along multiple imaginary grid lines on said surface of said anode, by jumping from grid line-to-grid line, and wherein said deflection unit is configured to move said electron beam along said multiple grid lines to simulate movement of a source grid to determine said phase shift.

28. An x-ray system comprising:
a radiation source located at a first side of an examination subject, that generates a beam of coherent x-ray radiation with a grid-like origin;
a phase grid located in a path of said beam at an opposite, second side of the examination subject, said phase grid comprising spaced-apart grid lines that diffract adjacent coherent rays in said beam to generate an interference pattern of the x-ray radiation in a predetermined energy range of the x-ray radiation dependent on a phase shift of the x-ray beam produced by tissue of the examination subject;
an analysis-detector system that detects at least said interference pattern generated by said phase grid relative to a local intensity distribution thereof, to determine a local phase shift;
said radiation source comprising an anode from which said beam of coherent x-ray radiation with a grid-like origin is emitted, said anode comprising regions with respectively different radiation emission characteristics proceeding in spaced-apart bands that are parallel to the grid lines of the phase grid;
a radiation detector that detects said x-ray radiation after attenuation thereof by said examination subject, said radiation detector emitting detector output signals representing said attenuation; and
an image reconstruction computer supplied with said detector output signals, configured to reconstruct a projection phase-contrast image of the examination subject therefrom.

29. An x-ray computed tomography system comprising:
a radiation source located at a first side of an examination subject, that generates a beam of coherent x-ray radiation with a grid-like origin;
a phase grid located in a path of said beam at an opposite, second side of the examination subject, said phase grid comprising spaced-apart grid lines that diffract adjacent coherent rays in said beam to generate an interference pattern of the x-ray radiation in a predetermined energy range of the x-ray radiation dependent on a phase shift of the x-ray beam produced by tissue of the examination subject;
an analysis-detector system that detects at least said interference pattern generated by said phase grid relative to a local intensity distribution thereof, to determine a local phase shift;
said radiation source comprising an anode from which said beam of coherent x-ray radiation with a grid-like origin is emitted, said anode comprising regions with respectively different radiation emission characteristics proceeding in spaced-apart bands that are parallel to the grid lines of the phase grid;
a radiation detector that detects said x-ray radiation after attenuation thereof by said examination subject, said radiation detector emitting detector output signals representing said attenuation;
a rotation unit selected from the group consisting of a C-arm and a gantry, at which said x-ray source and said radiation detector are mounted, that rotates said x-ray source and said radiation detector around the examination subject while irradiating the examination subject with said x-ray radiation and while detecting attenuation of the x-ray radiation by said subject with said radiation detector; and
an image computer supplied with said detector output signals configured to reconstruct an image of the examination subject therefrom, selected from the group consisting of projection phase-contrast images and tomographic phase contrast images.

30. A method for generating projection or tomographic phase contrast exposures of an examination subject using an x-ray apparatus, comprising the steps of:
emitting a beam of coherent x-ray radiation with a grid-like origin from an anode in a radiation source and irradiating a subject with said x-ray radiation from a first side of the examination subject;
generating an interference pattern with a phase grid located in a path of said beam at an opposite, second side of the examination subject, said phase grid comprising spaced-apart grid lines that diffract adjacent coherent rays in said beam to generate said interference pattern of the x-ray radiation in a predetermined energy range of the x-ray radiation dependent on a phase shift of the x-ray beam produced by tissue of the examination subject;

automatically detecting at least said interference pattern generated by said phase grid relative to a local intensity distribution thereof, to determine a local phase shift; and emitting said beam of coherent x-ray radiation with a grid-like origin from said anode by producing regions on said anode with respectively different radiation emission characteristics proceeding in spaced-apart bands that are parallel to the grid lines of the phase grid.

31. A method as claimed in claim 30 wherein said x-ray source comprises an electron beam emitter that emits an electron beam onto a focal spot of the anode, from which said x-ray radiation is emitted, and wherein said bands at said anode are located in said focal spot, said anode being comprised of anode base material and comprising producing said bands as bands on said anode comprised of a material different from said anode base material.

32. A method as claimed in claim 30 wherein said x-ray source comprises an electron source that emits an electron beam that strikes said anode at a focal spot, and comprising producing said bands as a plurality of adjacent, alternating lands and grooves located in said focal spot.

33. A method as claimed in claim 30 comprising rotatably mounting said anode in said x-ray source, forming a rotary anode.

34. A method as claimed in claim 33 wherein said x-ray source is an x-ray tube and comprising operating said x-ray tube with a tube current, and generating a stroboscopic pulsation of said tube current.

35. A method as claimed in claim 34 comprising matching a frequency and phase of the pulsation of the tube current to a rotation speed of the rotary anode to maintain a substantially constant position of said bands coinciding with a maximum of said tube current.

36. A method as claimed in claim 34 comprising matching a frequency and phase of said pulsation of the tube current to a rotation speed of said rotary anode to cause a position of said bands coinciding with a maximum of said tube current to migrate in steps in a rotation direction of said rotary anode, for measurement of said phase shift with a stationary phase grid and a stationary analysis grid.

37. A method as claimed in claim 30 wherein said x-ray source is an x-ray tube, and comprising emitting an electron beam onto said anode to cause said anode to emit said x-ray radiation with a grid-like origin, and producing said regions on said anode with respectively different radiation emission characteristics by deflecting said electron beam to cause said electron beam to move along at least one imaginary grid line on a surface of said anode.

38. A method as claimed in claim 37 comprising deflecting said electron beam to move along multiple imaginary grid lines on said surface of said anode, by jumping from grid line-to-grid line.

39. A method as claimed in claim 38 comprising deflecting said electron beam to move said electron beam along said multiple grid lines to simulate movement of a source grid to determine said phase shift.

* * * * *